(12) United States Patent
Belmkaddem (10) Patent No.: US 11,090,193 B2
(45) Date of Patent: Aug. 17, 2021

(54) REUSABLE SWAB

(71) Applicant: Zineb Belmkaddem, Owings, MD (US)

(72) Inventor: Zineb Belmkaddem, Owings, MD (US)

( * ) Notice: Subject to any disclaimer, the term of this patent is extended or adjusted under 35 U.S.C. 154(b) by 164 days.

(21) Appl. No.: 16/437,078

(22) Filed: Jun. 11, 2019

(65) Prior Publication Data

US 2020/0060877 A1    Feb. 27, 2020

Related U.S. Application Data

(60) Provisional application No. 62/720,712, filed on Aug. 21, 2018.

(51) Int. Cl.
*A61F 11/00* (2006.01)
*A47K 7/00* (2006.01)

(52) U.S. Cl.
CPC .............. *A61F 11/006* (2013.01); *A47K 7/00* (2013.01)

(58) Field of Classification Search
CPC ...... A61F 11/006; A61F 13/38; A61F 13/385; A61F 13/36; A47K 7/00
See application file for complete search history.

(56) References Cited

U.S. PATENT DOCUMENTS

| | | | | |
|---|---|---|---|---|
| 1,450,612 | A * | 4/1923 | Schultz | A61F 11/006 606/160 |
| 6,277,090 | B1 * | 8/2001 | Crawford, Jr. | A61F 13/38 15/176.2 |
| 6,450,724 | B1 * | 9/2002 | Cambio | B43M 11/08 401/183 |
| 7,951,106 | B1 * | 5/2011 | Perez | A61F 11/006 604/11 |
| 2003/0181840 | A1 * | 9/2003 | Tsaur | A61M 35/006 604/1 |
| 2007/0299457 | A1 * | 12/2007 | Morales | A61F 11/006 606/162 |
| 2018/0369022 | A1 * | 12/2018 | Khazaal | A61F 13/38 |

* cited by examiner

*Primary Examiner* — Jocelin C Tanner
(74) *Attorney, Agent, or Firm* — The Law Office of Michael E. Kondoudis

(57) ABSTRACT

A swab comprises a support structure, a first cap and a second cap. The support structure has a first end, a central portion and a second end. The first cap has a first cap end and a first open end, wherein the first cap end includes a first end outer surface, a first end inner surface and a first plurality of protrusions protruding from the first end outer surface. The second cap has a second cap end and a second open end, wherein the second cap end includes a second end outer surface and a second end inner surface. The support structure is insertable into the first open end such that the first end contacts the first end inner surface and is insertable into the second open end such that the second end contacts the second end inner surface.

18 Claims, 5 Drawing Sheets

REUSABLE SWAB

The present application claims priority from U.S. Provisional Application No. 62/720,712 filed Aug. 21, 2018, the entire disclosure of which is incorporated herein by reference.

BACKGROUND OF THE INVENTION

Embodiments of the disclosure relate to ear cleaning swabs.

There exists a need for a swab that is reusable.

SUMMARY OF THE INVENTION

Aspects of the present disclosure are drawn to a swab that includes a support structure, a first cap and a second cap. The support structure has a first end, a central portion and a second end. The central portion is disposed between the first end and the second end. The first end, the central portion and the second end are disposed along a central axis. The first cap has a first cap end and a first open end. The first cap end includes a first end outer surface, a first end inner surface and a first plurality of protrusions protruding from the first end outer surface. The second cap has a second cap end and a second open end. The second cap end includes a second end outer surface and a second end inner surface. The support structure is shaped such that the first end is insertable into the first open end and such that the first end contacts the first end inner surface. The support structure is additionally shaped such that the second end is insertable into the second open end and such that the second end contacts the second end inner surface.

BRIEF DESCRIPTION OF THE DRAWINGS

The accompanying drawings, which are incorporated in and form a part of the specification, illustrate example embodiments and, together with the description, serve to explain the principles of the disclosure. In the drawings.

DETAILED DESCRIPTION OF THE EMBODIMENTS

Ears are self-cleaning, and have a built-in natural mechanism of pushing dead skin cells, dirt, and excess cerumen out of the ear onto the ear opening. Conventional swab products either push cerumen in or dig too much out, both ill-advised and dangerous as they often could lead to worsening buildup or causing injuries. In addition, the finger and tissue ear cleaning process causes wax to stick to nails when tissue is punctured during the cleaning process.

The readily available mass market products more often than not go against expert physician guidelines, which insist on avoiding earwax removal from the ear canal. They are designed in a way small enough to allow unsafe penetration of the ear canal, usually rendering the warnings they include on their product labels ineffective. In fact, the Journal of Pediatrics reported approximately 34 injuries a day at emergency services directly due to the use of cotton swabs.

Further, most existing devices harm the environment by being, single-use and disposable, increasing plastics and toxin collecting cotton in oceans and our ecosystem, exposing marine life to harm, and potentially humans as well from fish-ingested microplastics and toxins.

A reusable swab in accordance with aspects of the present disclosure is designed to remove excess wax from the outer ear opening using soft protrusions, without prodding in the canal where harm can occur such as punctured ear drums.

A reusable swab in accordance with aspects of the present disclosure is a safe more effective alternative to environmentally unsustainable solutions, such as cotton swabs that pose a serious risk to oceans when flushed into waterways, and other means used to clean tissue, which are equally harmful to forests. Further, a reusable swab in accordance with aspects of the present disclosure keeps the fingers and nails clean, as well as bath towels and any other washcloths.

A reusable swab in accordance with aspects of the present disclosure ensures safety through its larger size, which does not allow it to penetrate the ear canal, but facilitates cleaning of outer ear wax and dead skin cells through collection by the reusable swab's soft protrusions. A reusable swab in accordance with aspects of the present disclosure is designed to remove excess wax from the outer ear opening using soft protrusions, without prodding in the canal where harm can occur such as punctured ear drums.

A reusable swab in accordance with aspects of the present disclosure solves existing problems by being reusable, immediately and conveniently washable after each use, and safe to use for children and for adults. Its design prevents reaching the inner ear canal and/or harming the eardrum. Protrusions of the reusable swab trap and wipe any excess cerumen from the outer ear. In addition, a reusable swab in accordance with aspects of the present disclosure can be used in the shower for convenience.

In a non-limiting example embodiment, a reusable safe silicon swab has silicon protrusions protruding from one or both ends of the swab. These protrusions allow collection of any wax that has been pushed out of the ear canal naturally. The swab ends are large enough to ensure they do not penetrate the ear canal or cause any injuries or harm. In addition, the protrusions allow safe washing and dead skin removal from the back of the ear as well as concha, fossa, scapha and helix.

In operation, an individual holds the swab from the middle, and uses one or both ends to collect earwax and dead skin cells from the ear canal opening, and from other parts of the ear, e.g., the scapha, the fossa and the concha. This is done by gently twisting and moving the swab as needed to allow the protrusions to collect as much outer earwax/dirt/dead skin cells as possible. The swab can be safely used during the shower, or after. A reusable swab in accordance with aspects of the present disclosure can also be used to clean other parts, non-limiting examples of which include the nostrils.

A reusable swab in accordance with aspects of the present disclosure prevents unsafe, excessive, deep harmful, ear wax cleaning for kids and adults.

Example embodiments of a reusable swab in accordance with aspects of the present disclosure will now be described in greater detail with reference to FIGS. 1A-7.

A first example embodiment of a reusable swab in accordance with aspects of the present disclosure will now be described in greater detail with reference to FIGS. 1A-B.

Figure 1A:
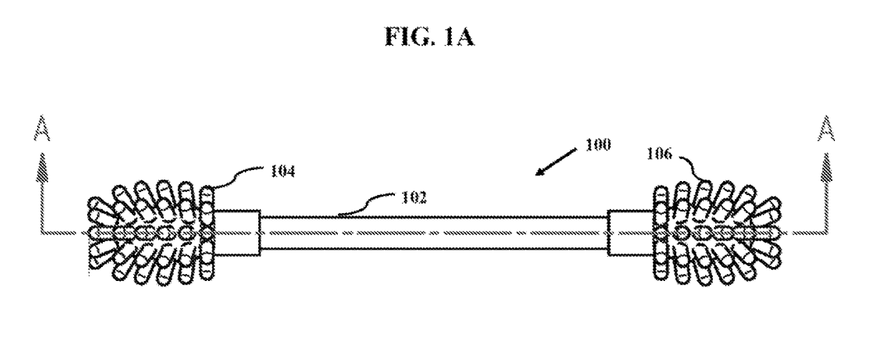
FIG. 1A illustrates a side view of a first embodiment of a reusable swab in accordance with aspects of the present disclosure.
Figure 1B:
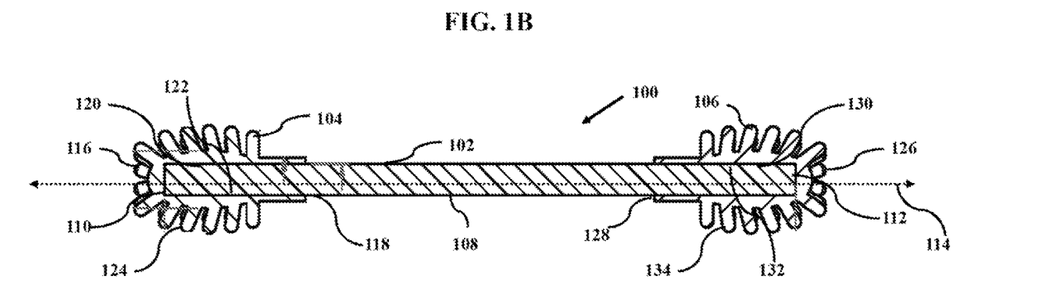
FIG. 1B illustrates a cross-sectional view of the reusable swab of FIG. 1A.

FIG. 1A illustrates a side view of a first embodiment of a reusable swab 100 in accordance with aspects of the present disclosure.

As shown in the figure, reusable swab 100 includes a support structure 102, a cap 104 and a cap 106.

FIG. 18 illustrates a cross-sectional view of reusable swab 101 of FIG. 1A, as cut along a dash-dotted line A-A.

As shown in the figure, support structure 102 includes a central portion 108, an end 110 and an end 112. Central portion 108 is disposed between end 110 and end 112. Further, end 110, central portion 108 and end 112 are disposed along an axis 114.

Cap 104 has a cap end 116, open end 118, an outer surface 120 and an inner surface 122. Outer surface 120 includes a plurality of protrusions, a sample of which is indicated as protrusion 124.

Cap 106 has a cap end 126, open end 128, an outer surface 130 and an inner surface 132. Outer surface 130 includes a plurality of protrusions, a sample of which is indicated as protrusion 134.

Support structure 102 is shaped such that end 110 is insertable into open end 118 of cap 104 and such that end 110 contacts inner surface 122 of cap 104. Support structure 102 is additionally shaped such that end 112 is insertable into open end 128 of cap 106 and such that end 112 contacts inner surface 132 of cap 106.

In an example embodiment, support structure 102 is cylindrically shaped.

In some embodiments, support structure 102 is shaped such that end 110 is removably insertable into open end 118 of cap 104. In these embodiments, cap 104 (and similarly cap 106) may be repeatedly removed from and replaced onto support structure 102. In some embodiments, cap 104 (and similarly cap 106) may be permanently affixed to support structure 102 by way of an adhesive being added between end 110 and cap 104 (and similarly an adhesive being added between end 112 and cap 106). In other embodiments, cap 104 (and similarly cap 106) may be permanently affixed to support structure 102 by way of overmolding cap 104 onto end 110 (and similarly overmolding cap 106 onto end 112).

In some embodiments, support structure 102 is additionally shaped such that end 112 is removably insertable into open end 128 of cap 106. In these embodiments, cap 106 may be repeatedly removed from and replaced onto support structure 102.

Support structure 102, cap 104 and cap 106 may comprise a material selected from a group of materials consisting of silicon, rubber, plastic, biodegradable material and combinations thereof. In some embodiments, support structure 102 comprises one type of material, wherein cap 104 and cap 106 comprise a different type of material than that of support structure 102. In some embodiments, support structure 102, cap 104 and cap 106 each comprise a different respective material.

Each or all of support structure 102, cap 104 and cap 106 may be fabricated by any known method, non-limiting examples of which include rapid prototyping, injection molding of silicon or similar materials, over molding, compression/transfer molding, and fabrication from a custom-made mold.

Cap 104 and cap 106 are designed to have a size that prevents insertion into the inner ear canal and/or harming the eardrum. The plurality of protrusions protruding from cap 104 and cap 106 allow collection of any wax that has been pushed out of the ear canal naturally. In addition, the plurality of protrusions protruding from cap 104 and cap 106 allow safe washing and dead skin removal front the back of the ear as well as concha, fossa, scapha and helix.

A protrusion of the plurality of protrusions may be any extension from the surface of a cap, have any known shape and be any size that permits at least two protrusions to protrude from a surface of a cap. Non-limiting examples of protrusions include bulges, bumps, humps, lumps, juts, prominences, protuberances, swells, projections and bristles.

In operation, an individual holds reusable swab 100 at support structure 102, and uses one of cap 104 and cap 106 to collect earwax and dead skin cells from the ear canal opening, and from other parts of the ear, e.g., the scapha, the fossa and the concha. This is done by gently twisting and moving reusable swab 100 as needed to allow the plurality of protrusions protruding from cap being used, i.e., either cap 104 or cap 106, to collect as much outer earwax/dirt/dead skin cells as possible. Reusable swab 100 can be safely used during the shower, or after.

It should be noted that the plurality of protrusions protruding from cap 104 and cap 106 in the example embodiment discussed above are similarly situated. In other embodiments, the plurality of protrusions protruding from cap 104 may be differently situated compared to those of cap 106. Further, in some embodiments, only one of cap 104 and cap 106 includes a plurality of protrusions. In some embodiments, one of cap 104 and cap 106 may be replaced with a cap that does not include protrusions.

In an example embodiment support structure 102 comprises a material that has a rigidity that is more rigid than the rigidity of cap 104 and cap 106, wherein cap 104 and cap 106 are more flexible and support structure 102. In this manner, cap 104 and cap 106 will more gently scrub tissue whereas support structure 102 will maintain support so that the user may apply pressure on the cap currently being used.

A second example embodiment of a reusable swab in accordance with aspects of the present disclosure will now be described in greater detail with reference to FIGS. 2-7.

Figure 2:
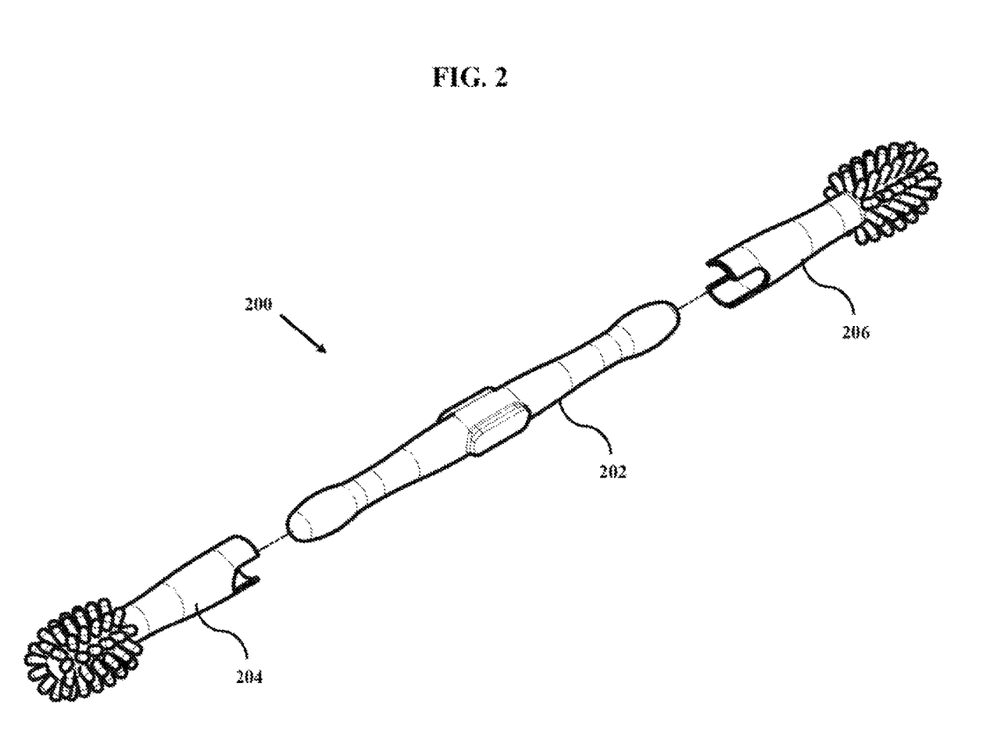
FIG. 2 illustrates an oblique view of components of a second embodiment of a reusable swab in accordance with aspects of the present disclosure.

FIG. 2 illustrates an oblique view of components of a second embodiment of a reusable swab 200 in accordance with aspects of the present disclosure.

As shown in the figure, reusable swab 200 includes a support structure 202, a cap 204 and a cap 206. In the figure, cap 204 and cap 206 are separated from support structure 202.

Figure 3:
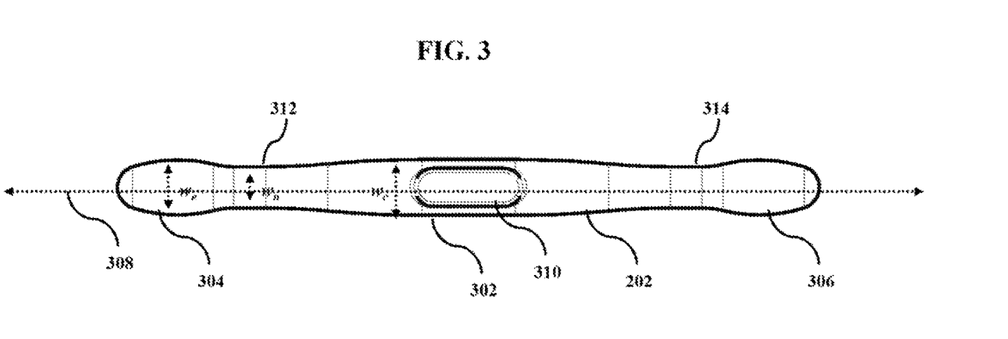
FIG. 3 illustrates a side view of a support structure the reusable swab of FIG. 2.

FIG. 3 illustrates a side view of support structure 202 of reusable swab 200.

As shown in the figure, support structure 202 includes a central portion 302, an end 304 and an end 306. Central portion 302 is disposed between end 304 and end 306. Further, end 304, central portion 302 and end 306 are disposed along an axis 308.

Central portion 302 includes a protrusions 310 that protrudes from one side and another protrusion (not shown) that protrudes on an opposite side of central portion 302. Central portion 302 is generally cylindrical in shape with a central width, $w_c$, but tapers at both ends into more narrow neck portions 312 and 314. Neck portions 312 and 314 have a neck width, $w_n$, that is more narrow than $w_e$. Neck portions 312 and 314 expand into end 304 and end 306, respectively.

Each of end 304 and 306 has a bulbous shape with a maximum end width, $w_e$, wherein $w_e$ is greater than $w_n$. In some embodiments, $w_e$ is equal $w_c$. In other embodiments, $w_e$ is less than $w_c$. In still other embodiments, $w_e$ is greater than $w_c$.

Figure 4:
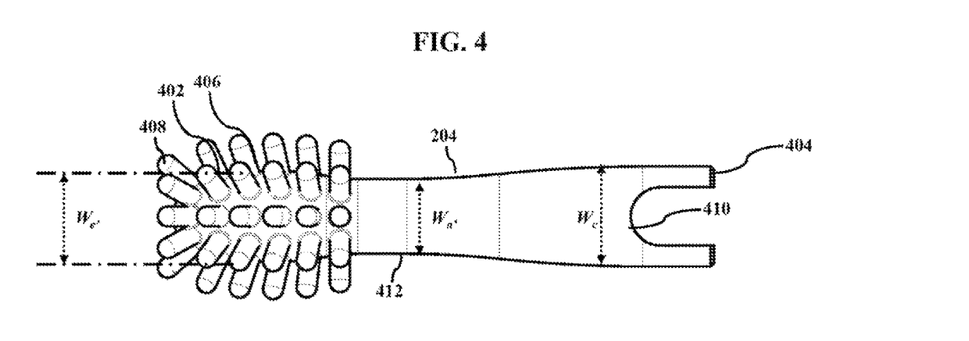
FIG. 4 illustrates a side view of a cap of the reusable swab of FIG. 2.

FIG. 4 illustrates a side view of cap 204 of reusable swab 200.

As shown in the figure, cap 204 has a cap end 402, open end 404 and an outer surface 406. Outer surface 406 includes a plurality of protrusions, a sample of which is indicated as protrusion 408. Open end 404 includes a u-shaped cut-out 410 and u-shaped cut-out (not shown) on an opposite side.

Cap end 402 has a bulbous shape with a maximum end width, $w_e'$ wherein $w_e'$ is slightly greater than $w_e$ of end 304 discussed above with reference to FIG. 3. Open end 404 has a cylindrical shape with an open end width, $w_c'$, wherein $w_c'$ is slightly greater than $w_c$ of central portion 302 discussed above with reference to FIG. 3. Open end 404 tapers to a middle portion 412 before expanding, to cap end 402. Middle portion 412 has middle width, $w_n'$, wherein $w_n'$ is slightly greater than $w_n$ of neck portion 312 discussed above with reference to FIG. 3

In some embodiments, when $w_e$ is equal to $w_e$, $w_e'$ is equal to $w_e'$. In other embodiments, when $w_e$ is, less than $w_c$, $w_e'$ is less than $w_e'$. In still other embodiments, when $w_e$ is greater $w_c$, $w_e'$ to is greater than $w_c'$.

Cap 206 has a similar structure to that of cap 204, and therefore will not be described in further detail for brevity.

Figure 5A:
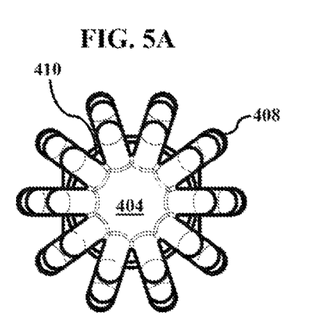
FIG. 5A illustrates side view of the protrusion end of a cap of the reusable swab of FIG. 2.

FIG. 5A illustrates side view of protrusion end 404 of cap 204 of reusable swab 200.

As shown in the figure, the plurality of protrusions are arranged in linear rows. It should be noted that this non-limiting example embodiment is illustrated for purposes of discussion and that the plurality of protrusions might be randomly arranged, or arranged in a non-linear fashion.

Figure 5B:
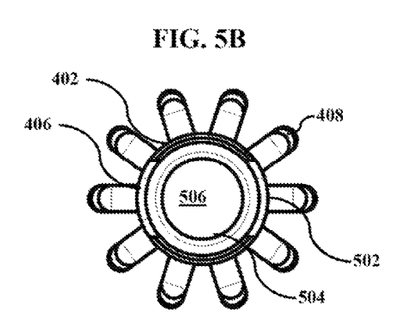
FIG. 5B illustrates side view of the open end of the cap of the reusable swab of FIG. 2.

FIG. 5B illustrates side view of open end 402 of cap 204 of reusable swab 200.

As shown in the figure, cap 204 includes an inner surface 504 that surrounds the entirety of an open volume 506.

It should be noted that the plurality of protrusions protruding from cap 204 and cap 206 in the example embodiment discussed above are similarly situated. In other embodiments, the plurality of protrusions protruding from cap 204 may be differently situated compared to those of cap 206. Further, in some embodiments, only one of cap 204 and cap 206 includes a plurality of protrusion. In some embodiments, one of cap 204 and cap 206 may be replaced with a cap that does not include protrusions.

In an example embodiment support structure 202 comprises a material that has a rigidity that is more rigid than the rigidity of cap 204 and cap 206, wherein cap 204 and cap 206 are more flexible and support structure 202. In this manner, cap 204 and cap 206 will more gently scrub tissue whereas support structure 202 will maintain support so that the user may apply pressure on the cap currently being used.

As shown in FIGS. 2-5B, support structure 202 is shaped such that end 304 is insertable into open end 404 of cap 206 and such that end 304 contacts inner surface 504 of cap 206. Support structure 202 is additionally shaped such that end 306 is insertable into the open end of cap 206 and such that end 306 contacts the inner surface of cap 206.

In particular, support structure 202 comprises a material that has a rigidity that is more rigid than the rigidity of cap 204 and cap 206. Cap 204 and cap 206 are more flexible and support structure 202.

Returning to FIGS. 2-4, when support structure 202 is inserted into cap 204, end 304 of support structure 202 enters open end 404 of cap 204 and continues to middle portion 412 of cap 204. As end 304 of support structure 202 contacts middle portion 412, end 304 of support structure 202 continues through middle portion 412, which expands because of its flexibility. As end 304 of support structure 202 continues to press through middle portion 412, end 304 continues through middle portion 412 until end 304 passes middle portion 412 and enters into the volume surrounded by cap end 402. At that point middle portion 412 of cap 204 will have contracted to its original shape, which corresponds to the shape of narrow neck portion 312 of support structure 202.

Further, as support structure 202 is inserted into cap 204, 410 will engage with 310. Similarly, the other cut-out (not shown) on 204 will engage with the corresponding other protrusion (not shown) on 202.

Support structure 202 is inserted into cap 206 in a manner similar to that discussed above with reference to cap 204.

Figure 6:
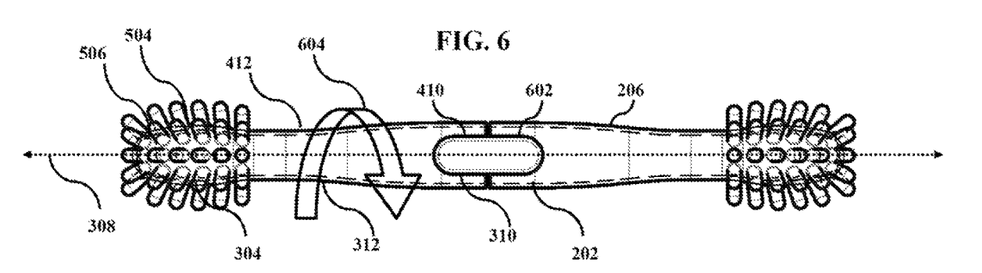
FIG. 6 illustrates a side view of the assembled reusable swab of FIG. 2.

FIG. 6 illustrates a side view of assembled reusable swab 200.

As shown in the figure, when support structure 202 is fully inserted into cap 204, end 304 of support structure 202 fills volume 506 of cap 204 and neck portion 312 of support structure 202 contacts middle portion 412 of cap 204 and u-shaped cut-out 410 of cap 204 engages with protrusion 310 of support structure 202. The arrangement of support structure 202 with cap 206 preferably is the same.

Because end 304 of support structure 202 is much wider than middle portion 412 of cap 204, support structure 202 will not become disengaged from cap 204 unless the user intentionally pulls cap 204 off with sufficient force. This male/female engaging structure prevents cap 204 from falling off support structure 202 unintentionally. This same feature applied to cap 206.

Further, when support structure 202 is fully inserted into cap 204, u-shaped cut-out 410 of cap 204 engages with protrusion MO of support structure 202. The arrangement of support structure 202 with cap 206 is the same.

Because u-shaped cut-out 410 of cap 204 engages with protrusion 310 of support structure 202, cap 204 cannot rotate about axis 308 (as shown by arrow 604) independently from support structure 202. However, cap 204 can rotate about axis 308 (as shown by arrow 604) with support structure 202. Cap 206 is similarly prevented from rotating independently from support structure 202. Further, because of the dual engagement of cap 204 and cap 206 with protrusion 310, cap 206 is prevented from rotating independently from cap 204. With this engagement structure between protrusion 310 and the caps, a user may grasp any portion of reusable swab 200, rotate reusable swab 200 and the cap that is currently being used to clean will rotate accordingly.

Figure 7:
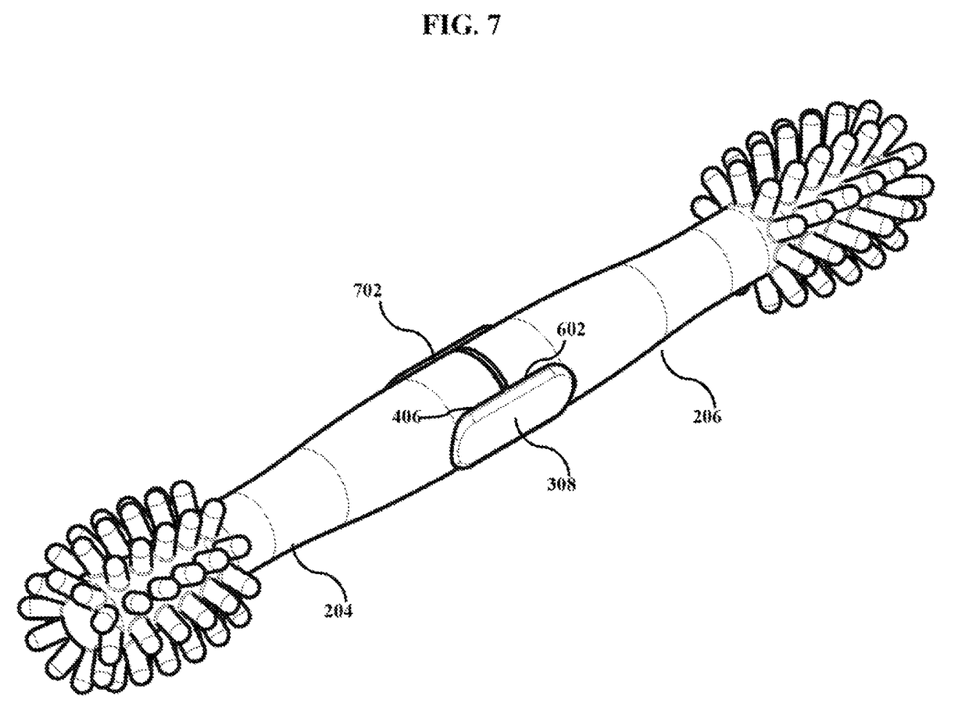
FIG. 7 illustrates an oblique view of the assembled reusable swab of FIG. 2.

FIG. 7 illustrates an oblique view of assembled reusable swab 200.

In the non-limiting example embodiment discussed above with reference to FIGS. 2-7, protrusion 310 has an oval or substantially oval shape and the corresponding cut-outs on the caps have a u-shape to engage with protrusion 310. It should be noted that a protrusion on a support structure in accordance with aspects of the present disclosure may have any shape, so long the cut-outs in the caps have a corresponding shape that may engage with the protrusion.

In the non-limiting example embodiment discussed above with reference to FIGS. 2-7, support structure 202 has two protrusions to engage with the caps. It should be noted that a support structure in accordance with aspects of the present disclosure may have any integer number of protrusions, so long at least one cut-outs in each cap have a corresponding shape that may engage with at least one of the integer number of protrusions.

The foregoing description of various embodiments have been presented for purposes of illustration and description. It is not intended to be exhaustive or to limit the disclosure to the precise forms disclosed, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

What is claimed as new and desired to be protected by Letters Patent of the United States is:

1. A swab comprising:
    a support structure having a first end, a central portion, and a second end, said central portion being disposed between said first end and said second end, said first end, said central portion and said second end being disposed along a central axis;
    a first cap having a first cap end and a first open end, said first cap end including a first end outer surface, a first end inner surface and a first plurality of protrusions protruding from said first end outer surface; and
    a second cap having a second cap end and a second open end, said second cap end including a second end outer surface and a second end inner surface,
    wherein said support structure is shaped such that said first end is insertable into said first open end and such that said first end contacts said first end inner surface,
    wherein said support structure is additionally shaped such that said second end is insertable into said second open end and such that said second end contacts said second end inner surface,
    wherein said support structure is shaped such that said first end is removeably insertable into said first open end,
    wherein said support structure is additionally shaped such that said second end is removeably insertable into said second open end,
    wherein said central portion includes a central engaging portion,
    wherein said first open end has a first end engaging portion,
    wherein said second open end has a second end engaging portion,
    wherein said support structure is shaped such that said first end is removably insertable into said first open end and such that said central engaging portion engages said first end engaging portion so as to prevent rotation of said first cap with reference to said support structure about the central axis, and
    wherein said support structure is additionally shaped such that said second end is removeably insertable into said second open end and such that said central engaging portion engages said second end engaging portion so as to prevent rotation of said second cap with reference to said support structure about the central axis.

2. The swab of claim 1,
    wherein said central engaging portion comprises a protrusion,
    wherein said first end engaging portion comprises a first u-shaped cut-out that is operable to engage with said protrusion, and
    wherein said second end engaging portion comprises a second u-shaped cut-out that is operable to engage with said protrusion.

3. The swab of claim 2,
    wherein said protrusion is disposed on a side of said central portion,
    wherein said central engaging portion farther comprises a second protrusion disposal on an opposite side of said central portion with reference to said side of said central portion,
    wherein said first end engaging portion comprises a third u-shaped cut-out that is operable to engage with said second protrusion, and
    wherein said second end engaging portion comprises a fourth u-shaped cut-out that is operable to engage with said second protrusion.

4. The swab of claim 3, wherein said second cap, end additionally includes a second plurality of protrusions protruding from said second end outer surface.

5. The swab of claim 4, wherein said first cap and said second cap comprise a material selected from a group of materials consisting of silicon, rubber, plastic, biodegradable material, and combinations thereof.

6. The swab of claim 5,
    wherein said support structure comprises a first material, and
    wherein said first cap and said second cap comprises a second material that is different from said first material.

7. The swab of claim 2, wherein said second cap end additionally includes a second plurality of protrusions protruding from said second end outer surface.

8. The swab of claim 7, wherein said first cap and said second cap comprise a material selected from a group of materials consisting of silicon, rubber, plastic, biodegradable material, and combinations thereof.

9. The swab of claim 8,
    wherein said support structure comprises a first material, and
    wherein said first cap and said second cap comprises a second material that is different from said first material.

10. The swab of claim 1, wherein said second cap end additionally includes a second plurality of protrusions protruding from said second end outer surface.

11. The swab of claim 10, wherein said first cap and said second cap comprise a material selected from a group of materials consisting of silicon, rubber, plastic and combinations thereof.

12. The swab of claim 11,
    wherein said support structure comprises a first material, and
    wherein said first cap and said second cap comprises a second material that is different from said first material.

13. The swab of claim 1, wherein said second cap end additionally includes a second plurality of protrusions protruding from said second end outer surface.

14. The swab of claim 13, wherein said first cap and said second cap comprise a material selected from a group of materials consisting of silicon, rubber, plastic and combinations thereof.

15. The swab of claim 14,
wherein said support structure comprises a first material, and
wherein said first cap and said second cap comprises a second material that is different from said first material.

16. The swab of claim 1, wherein said first cap and said second cap comprise a material selected from a group of materials consisting of silicon, rubber, plastic and combinations thereof.

17. The swab of claim 16,
wherein said support structure comprises a first material, and
wherein said first cap and said second cap comprises a second material that is different from said first material.

18. The swab of claim 1,
wherein said support structure comprises a first material, and
wherein said first cap and said second cap comprises a second material that is different from said first material.

\* \* \* \* \*